(12) United States Patent
Takai et al.

(10) Patent No.: US 8,013,200 B2
(45) Date of Patent: Sep. 6, 2011

(54) PROCESS FOR PRODUCING OLEFINS

(75) Inventors: Toshihiro Takai, Nishinomiya (JP);
Hirokazu Ikenaga, Ichihara (JP);
Makoto Kotani, Yokohama (JP);
Shigeaki Fujii, Sennan (JP)

(73) Assignee: Mitsui Chemicals, Inc., Minato-ku, Tokyo (JP)

( * ) Notice: Subject to any disclaimer, the term of this patent is extended or adjusted under 35 U.S.C. 154(b) by 0 days.

(21) Appl. No.: 12/597,366

(22) PCT Filed: Apr. 18, 2008

(86) PCT No.: PCT/JP2008/057578
§ 371 (c)(1),
(2), (4) Date: Oct. 23, 2009

(87) PCT Pub. No.: WO2008/136280
PCT Pub. Date: Nov. 13, 2008

(65) Prior Publication Data
US 2010/0063339 A1 Mar. 11, 2010

(30) Foreign Application Priority Data

Apr. 27, 2007 (JP) ................................. 2007-118891

(51) Int. Cl.
*C07C 6/04* (2006.01)
(52) U.S. Cl. ......... 585/646; 585/500; 585/643; 585/647
(58) Field of Classification Search .................. 585/643, 585/646, 647, 500
See application file for complete search history.

(56) References Cited

U.S. PATENT DOCUMENTS

| 3,536,777 A |   | 10/1970 | Alkema et al. |         |
|-------------|---|---------|---------------|---------|
| 3,786,112 A | * | 1/1974  | Reusser et al. | 585/644 |
| 3,865,751 A | * | 2/1975  | Banks et al.  | 502/251 |
| 4,511,672 A | * | 4/1985  | Hobbs         | 502/243 |

(Continued)

FOREIGN PATENT DOCUMENTS

CA 862816 * 2/1971

(Continued)

OTHER PUBLICATIONS

Banks, et al., "New Developments and Concepts in Enhancing Activities of Heterogeneous Metathesis Catalysts" in J. Molecular Catalysis, 28 (1985), 117-131.*

(Continued)

*Primary Examiner* — In Suk Bullock
*Assistant Examiner* — Bradley Etherton
(74) *Attorney, Agent, or Firm* — Rankin, Hill & Clark LLP

(57) ABSTRACT

In a process for producing olefins by a metathesis reaction comprising feeding an olefin gas to pass the olefin through a catalyst bed in the presence of hydrogen gas to convert the olefin into another kind of olefin, the catalyst bed having a catalyst including at least one metal selected from the group consisting of tungsten, molybdenum, rhenium, niobium, tantalum and vanadium, and a co-catalyst including a basic compound having at least one metal selected from the group consisting of Group Ia (alkali metals), Group IIa (alkaline earth metals), Group IIb and Group IIIa of the periodic table, the improvement lies in controlling the superficial velocity of the gas passing through the catalyst bed to 0.01 to 2.0 m/sec. According to the present invention, the presence of hydrogen gas dramatically increases the durability of the metathesis catalytic activity and the by-production of paraffins is suppressed.

7 Claims, 1 Drawing Sheet

U.S. PATENT DOCUMENTS

| | | | |
|---|---|---|---|
| 4,575,575 A | 3/1986 | Drake et al. | |
| 4,684,760 A | 8/1987 | Drake | |
| 4,754,098 A | 6/1988 | Drake | |
| 5,300,718 A * | 4/1994 | McCaulley | 585/324 |
| 5,304,692 A * | 4/1994 | Yamada et al. | 585/646 |

FOREIGN PATENT DOCUMENTS

| | | |
|---|---|---|
| JP | 4816482 | 5/1973 |
| JP | 5713532 | 3/1982 |
| JP | 59-001430 | 1/1984 |
| WO | 2006093058 | 9/2006 |

OTHER PUBLICATIONS

NIST Data, 1-butene physical property data available on-line at http://webbook.nist.gov.*

International Search Report for PCT/JP2008/057578 dated Jun. 10, 2008.

Elsevier Sequoia; Journal of Molecular Catalysis; vol. 28 No. 1-3; Jan. 1985; pp. 117-131.

* cited by examiner

PROCESS FOR PRODUCING OLEFINS

FIELD OF THE INVENTION

The present invention relates to an olefin production process capable of efficiently converting starting olefins into other kinds of olefins by metathesis reaction in the presence of hydrogen gas.

BACKGROUND OF THE INVENTION

Naphtha cracking produces various hydrocarbon compounds such as ethylene, propylene and butene, and the production percentages of these olefins are inevitably fixed. The proportions in which these olefins are produced are not always in agreement with the olefin demands. It is therefore necessary that the olefins from the naphtha cracking are converted to meet the demands. Metathesis reaction is used for the conversion of olefins. In the metathesis reaction, olefins of the same or different kinds are reacted with each other to yield olefins having different structures. The reaction is of high importance because it is capable of converting the olefins from the naphtha cracking in response to changes in olefin demands.

In 1931, it was found that the olefin metathesis reaction proceeded at a high temperature of 725° C. without catalysts. However, it was not until the development of a catalyst having an oxide of metal such as molybdenum, tungsten or rhenium supported on a large-surface area carrier that the industrial value of the metathesis reaction was acknowledged. The first metathesis reaction with such catalysts was developed by Phillips Petroleum Company in 1964 wherein ethylene and 2-butene were synthesized from propylene under catalysis of molybdenum oxide supported on γ-alumina.

The metathesis reaction is reversible, and thus there exists an equilibrium composition. For example, in the metathesis reaction of ethylene and 2-butene into propylene, the equilibrium shifts such that more propylene is produced at lower temperatures. Studies have been then carried out to lower the reaction temperature by improving catalysts. Phillips Petroleum Company developed a method wherein a catalyst comprising tungsten oxide supported on silica, and co-catalyst magnesium oxide are used in combination. This method has been established as a propylene production process by Lummus Global, Inc.

In particular, U.S. Pat. No. 4,575,575 (Patent Document 1) and Journal of Molecular Catalysis, Vol. 28, p. 117 (1985) (Non-Patent Document 1) report that when a metathesis reaction between ethylene and 2-butene is carried out at 330° C. in the presence of silica-supported tungsten oxide as a catalyst, the conversion of butene is only 31%, while when magnesium oxide is used in combination as a co-catalyst, the conversion is enhanced to 67%.

Moreover, U.S. Pat. No. 4,754,098 (Patent Document 2) reports that in the same metathesis reaction at 330° C., the use of a co-catalyst in which magnesium oxide is supported on γ-alumina increases the conversion of butene to 75%. It is also reported in U.S. Pat. No. 4,684,760 (Patent Document 3) that when a co-catalyst comprising magnesium oxide and lithium hydroxide supported on γ-alumina is used, the butene conversion is maintained at 74% even at a lower temperature of 270° C.

However, the reaction temperatures described in the above documents (for example, 270° C. in Patent Document 3) are still high considering the practical industrial process, and there are needed facilities such as heating furnaces in order to achieve such reaction temperatures, for example 270° C. The reaction temperature in the metathesis reaction should be therefore lowered to a level that is more simply achievable by steam heating, for example, approximately 200° C.

To solve this problem, the present applicant has already found that a silica-supported tungsten oxide catalyst in combination with a co-catalyst that is magnesium oxide or a system in which sodium hydroxide is supported on γ-alumina achieve a drastically improved catalytic activity in the presence of a small amount of hydrogen in the reaction (Patent Document 4). According to this method, the reaction temperature is lowered and propylene can be produced with much higher selectivity. Moreover, provided that the reaction temperature is constant, propylene can be stably produced for a longer time of period.

However, the above method requires the presence of hydrogen, although the amount thereof is small. The hydrogen undergoes undesired reactions with ethylene or propylene, resulting in by-production of ethane or propane.

Propane that is by-produced in the above reaction reduces the purity of propylene produced. The by-production of ethane causes process problems, i.e., when unreacted ethylene is recycled into the reactor, the ethane is concentrated and accumulated in the system.

JP-B-S48-16482 (Patent Document 5) and JP-B-S57-13532 (Patent Document 6) describe that hydrogen is used in the metathesis reaction in the presence of a catalyst in which molybdenum oxide and rhenium oxide are supported on alumina. These patent documents do not address the formation of by-products by hydrogenation, and are silent on superficial velocity.

[Patent Document 1] U.S. Pat. No. 4,575,575
[Patent Document 2] U.S. Pat. No. 4,754,098
[Patent Document 3] U.S. Pat. No. 4,684,760
[Patent Document 4] WO 2006/093058
[Patent Document 5] JP-B-S48-16482
[Patent Document 6] JP-B-S57-13532
[Non-Patent Document 1] Journal of Molecular Catalysis, Vol. 28, p. 117 (1985)

SUMMARY OF THE INVENTION

It is an object of the present invention to provide a metathesis reaction process for efficiently producing olefins in the presence of hydrogen gas while suppressing the by-production of paraffins.

In a process for producing olefins by a metathesis reaction comprising feeding an olefin gas to pass the olefin through a catalyst bed in the presence of hydrogen gas to convert the olefin into another kind of olefin, the catalyst bed comprising a catalyst including at least one metal selected from the group consisting of tungsten, molybdenum, rhenium, niobium, tantalum and vanadium, and a co-catalyst including a basic compound having at least one metal selected from the group consisting of Group Ia (alkali metals), Group IIa (alkaline earth metals), Group IIb and Group IIIa of the periodic table, the improvement comprises controlling the superficial velocity of the gas passing through the catalyst bed to 0.01 to 2.0 m/sec.

In the general metathesis reaction, the superficial velocity through a catalyst bed is usually about 0.001 m/sec to ensure a sufficient contact time with the catalyst. It has been found, however, that at such a low velocity, the olefins react with the hydrogen gas under the catalysis of the catalyst to yield paraffins. The present inventors have found that the conversion of olefins by the metathesis reaction does not require a long contact time with the catalyst. In the present invention, the gas is passed through the catalyst bed at a very high superficial velocity in the range of 0.01 to 2.0 m/sec. By bringing the olefins into contact with the catalyst in this manner, target olefins are produced efficiently while suppressing the formation of by-products such as paraffins. In detail, in the metathesis reaction of ethylene and 2-butene, controlling the superficial velocity of the gas through the catalyst bed at 0.01 to 2.0 m/sec enables efficient formation of the target propylene and reduces the amount of by-produced paraffins such as ethane and propane.

ADVANTAGES OF THE INVENTION

According to the olefin production process of the present invention, the gas is passed at a high superficial velocity, and therefore the starting olefins and hydrogen gas are in contact with the metathesis reaction catalyst for a short time. The contact time is such that the olefins are converted into other kinds of olefins but the hydrogenation of the olefins is suppressed. Thus, the undesired formation of paraffins in the reaction is prevented.

BEST MODE FOR CARRYING OUT THE INVENTION

Figure 1:
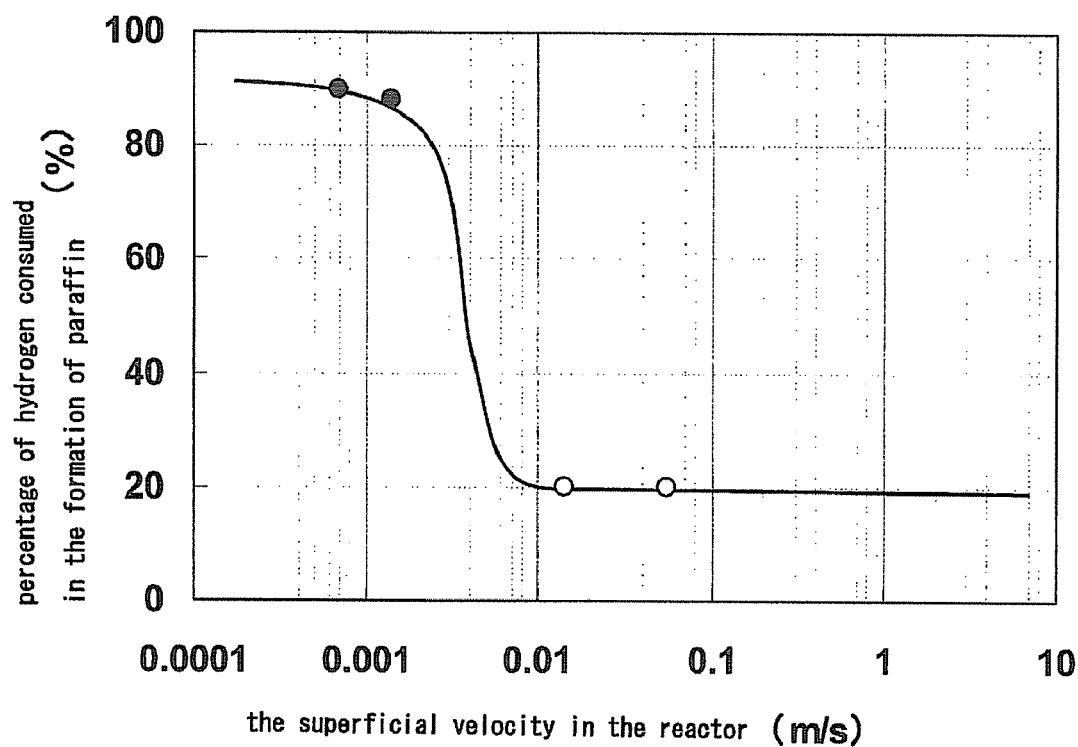
FIG. 1 is a graph showing the relationship between the superficial velocity in the reactor and the amount of hydrogen consumed in the formation of paraffins, according to Examples 1 and 2 and Comparative Examples 3 and 5.

The production of olefins by the metathesis reaction according to the present invention will be described in detail.

In the process for producing olefins by the metathesis reaction in the present invention, a catalyst and a co-catalyst are used in combination.

The catalyst used in the invention contains at least one metal selected from tungsten, molybdenum, rhenium, niobium, tantalum and vanadium. Of these, tungsten, molybdenum and rhenium provide relatively high catalytic activity. In particular, the catalyst having tungsten shows higher activity.

The metallic catalyst may be an oxide, sulfide or hydroxide of the metal. These may be used singly or two or more kinds may be used in combination. The metal compound may be supported on a carrier. The metathesis reaction catalyzed by the above catalyst is preferably a fixed-bed flow reaction. In the fixed-bed flow reaction, the catalyst is preferably an oxide of the metal because the deactivated catalyst may be regenerated by calcination.

The carrier for the catalyst preferably has a large surface area, usually not less than 10 m$^2$/g. The carrier is preferably a non-acidic compound because an acidic carrier induces oligomerization of olefins.

Examples of the carriers include silica, γ-alumina and titania, with silica being preferable because of large surface area. In the use of silica as the carrier, the amount of the metal supported in terms of oxide is preferably in the range of 0.01 to 50 wt %, and more preferably in the range of 0.1 to 20 wt % relative to the carrier.

The metal compound (catalyst) may be supported on the carrier by various methods. An exemplary method in the case of nitrate or hydroxide of the metal, or tungsten, molybdenum or rhenium is described: A polyacid or an isopolyacid of the metal compound or metal, or an ammonium salt of the polyacid, or an ammonium salt of the isopolyacid is used as a starting material. The starting material is formed into an aqueous solution, and the carrier is soaked therein. The solution is then evaporated to dryness, and the residue is calcined at a temperature of 300° C. or higher in an oxygen atmosphere.

As the carrier used herein, a commercially available carrier may be used without modification. Use is also possible of a carrier that is obtained by reacting a salt of a corresponding metal with a base and calcining the resulting hydroxide into an oxide.

When the carrier is prepared from a corresponding metal salt, a coprecipitation method may be used in which a metal salt which will form the catalyst is added together with the metal salt for the carrier and the synthesis of the carrier and the supporting of the metal compound catalyst are simultaneously carried out.

The carrier is generally formed into various shapes such as spherical shapes, cylindrical shapes, extruded shapes and crushed shapes. The size of the shaped particles is not limited as long as the particles can fill a metathesis reactor, and is generally in the range of 0.01 to 100 mm.

In the present invention, the above catalyst is used in combination with a co-catalyst. Examples of the co-catalysts used in the invention include compounds of metal elements belonging to Group Ia (alkali metals), Group IIa (alkaline earth metals), Group IIb and Group IIIa of the periodic table. These compounds may be used singly or two or more kinds may be used in combination. Of the metals in the Groups of the periodic table, lithium, sodium, potassium, cesium, magnesium, calcium, strontium, barium, zinc and yttrium are preferred.

U.S. Pat. Nos. 4,575,575, 4,754,098 and 4,684,760 (to Phillips Petroleum Company) describe that magnesium oxide is essentially used as a co-catalyst. In the present invention, magnesium oxide is not necessarily essential and may be replaced by or may be used in combination with compounds of metals such as lithium, sodium and potassium in view of catalytic activity for the metathesis reaction. These compounds may be used singly or two or more kinds may be used in combination.

The co-catalyst may be in a solid state such as oxide, hydroxide, nitrate or acetate. Such metal compounds may further contain other metals. Examples of such co-catalysts with other metals include hydrotalcite that is a layered double hydroxide of aluminum and magnesium, and a solid solution of aluminum oxide and magnesium oxide obtained by calcining the hydrotalcite. The oxides, mixed oxides, hydroxides, double hydroxides, nitrates and acetates of the metals may be supported on carriers having a large surface area.

The carrier for the co-catalyst is preferably a compound that does not show acidity even after the co-catalyst is supported thereon, because an acidic carrier may induce oligomerization of olefins.

Preferred examples of the carriers for the co-catalysts include γ-alumina, zirconia and titania. They may be used singly or two or more kinds may be used in combination. The surface area of the carrier is preferably not less than 10 m$^2$/g.

In the present invention, magnesium oxide may be used as a carrier for the co-catalyst because of its large surface area. Use is also possible of magnesium oxide and the above-described metal oxides in combination. In particular, the combination of γ-alumina and magnesium oxide is preferable because of high chemical stability of γ-alumina. A composite oxide of aluminum and magnesium is also usable.

In the use of the co-catalyst supported on the carrier, the amount of the co-catalyst metal in terms of oxide relative to the carrier is generally in the range of 0.01 to 50 wt %, and is preferably in the range of 0.1 to 20 wt %.

As the carrier for the co-catalyst, a commercially available carrier may be used without modification. Use is also possible of a carrier that is obtained by reacting a salt of a corresponding metal with a base by a known method and calcining the resulting hydroxide into an oxide.

Of the metal compounds as the co-catalysts, for example the oxides may be supported on the carrier by known methods. In an exemplary method, a nitrate or hydroxide of the metal is formed into an aqueous solution or suspension, and the carrier is soaked therein. The solution or suspension is then evaporated to dryness, and the residue is calcined at a temperature of 300° C. or higher in an air atmosphere.

When the carrier is prepared from a corresponding metal salt, a coprecipitation method may be used in which a metal salt which will form the co-catalyst is added together with the metal salt for the carrier and the synthesis of the carrier and the supporting of the metal compound co-catalyst are simultaneously carried out.

The shapes of the co-catalyst and the carrier for the co-catalyst are not particularly limited. These are generally formed into various shapes such as spherical shapes, cylindrical shapes, extruded shapes and crushed shapes. The size of the shaped particles is not limited as long as the particles can fill a metathesis reactor, and is generally in the range of 0.01 to 100 mm.

In the present invention, the metathesis reaction may be catalyzed by a catalyst system in which the metathesis reaction catalyst (metal(s) selected from tungsten, molybdenum, rhenium, niobium, tantalum and vanadium) and the co-catalyst (metal(s) selected from Group Ia (alkali metals), Group IIa (alkaline earth metals), Group IIb and Group IIIa of the periodic table) are supported on the carrier together.

In the metathesis reaction, the amount of the co-catalyst relative to the catalyst (co-catalyst/catalyst weight ratio) is generally from 0.1 to 20. When the ratio is below the range, the hydrogen gas that is added in a small amount in the metathesis reaction will not produce sufficient effects. When the ratio exceeds the range, the amount of the catalyst is too small relative to the total of the catalyst and the co-catalyst, and the catalytic activity is noticeably reduced.

The activity of the metathesis catalyst is drastically decreased by moisture contained in the catalyst, carbon dioxide, carbon monoxide, diene compounds, mercapto compounds, alcohols and carboxylic compounds. Accordingly, the olefins used as the starting materials preferably should not contain such components detrimental to the catalytic activity. Such impurities are preferably removed by sufficiently purifying the starting olefins by distillation, adsorption, extraction or washing before contact with the metathesis reaction catalyst. Excessive purification adds costs, and therefore the purification of the starting olefins is preferably performed to satisfy both the activity sustainability of the metathesis catalyst and the costs for the purification of the raw materials.

Other materials such as nitrogen gas and hydrogen gas that are introduced into the reactor are preferably as pure as possible.

The catalyst and the co-catalyst are generally placed in a cylindrical reactor. The upper and lower end portions of the reactor are filled with α-alumina balls or the like to hold the catalyst and the co-catalyst in the middle of the reactor.

It is often the case that the catalyst and the co-catalyst placed in the reactor contain a very small amount of water. Such water drastically reduces the catalytic activity in the metathesis reaction, and is therefore preferably removed before the starting olefins are fed. For example, the catalyst and the co-catalyst placed in the reactor may be exposed to the passage of an inert gas such as helium, nitrogen, argon or xenon that is heated to 300° C. or above for at least 10 minutes, whereby the moisture adsorbed to the catalyst, the co-catalyst, the carriers, and the α-alumina balls is removed.

The flowing of the heated inert gas is generally followed by reducing treatment to activate the catalyst by passing a heated reducing gas. The reducing gases used herein include carbon monoxide and hydrogen. The reducing gas is generally heated to not less than 300° C. and is passed for at least 10 minutes. In the production of olefins by the metathesis reaction in the present invention, olefins are converted in the presence of a small amount of hydrogen gas. Therefore, even if a small amount of hydrogen used as the reducing gas remains in the metathesis reactor, such residual hydrogen gas does not substantially reduce the reaction yield in the metathesis reaction.

In the present invention, olefins are brought into contact with the metathesis catalyst and co-catalyst that are pretreated as described above, whereby the olefins are converted into other kinds of olefins.

The starting olefins used in the metathesis reaction may be the same or different compounds from each other. In the olefin production by the metathesis reaction in the invention, a mixture of olefins from the naphtha cracking may be used.

The olefins used in the metathesis reaction in the invention are lower olefins. Examples of the olefins include ethylene, propylene, 1-butene, 2-butene, 2-pentene, 2-hexene, 4-methyl-2-pentene and 3-methyl-1-butene. These may be used singly or two or more kinds may be used in combination.

For example, there may be produced propylene from ethylene and 2-butene; propylene and 1-butene from ethylene and 2-pentene; propylene and 1-pentene from ethylene and 2-hexene; propylene and isobutene from ethylene and 2-methyl-2-butene; and propylene and 3-methyl-1-butene from ethylene and 4-methyl-2-pentene. Since the metathesis reaction is reversible, selecting the reaction conditions enables producing the starting olefins from the olefins produced in the above exemplary reactions.

When two or more kinds of olefins are used in the metathesis reaction to give another olefin, the molar ratio of the olefins in the starting materials is not particularly limited. When ethylene is included in the two or more kinds of olefins, the amount of ethylene is preferably in excess over the other olefins. In the case of the reaction of ethylene and 2-butene to produce propylene, the molar ratio of ethylene to n-butene (total of 1-butene and 2-butene) (ethylene/n-butene) is generally 1 to 50, and preferably about 1 to 5. When the ratio is too small, the reaction will preferentially take place between the butene molecules. When the ratio is too large, large facilities and energy are required to recover unreacted ethylene.

In the olefin production by the metathesis reaction, the starting olefins may be brought into contact with the metathesis catalyst and co-catalyst that form a fixed bed, a fluidized bed, a suspended bed or a staged fixed bed.

When a fixed-bed flow apparatus is packed with the catalysts, as described in the Journal of Molecular Catalysis, Vol. 28, p. 117 (1985), the catalyst and the co-catalyst may be physically mixed and placed in the apparatus, or the co-catalyst and the catalyst may be placed in this order along the direction in which the material gas is passed. These packing methods may be used in combination.

In the olefin production by the metathesis reaction, the gas is passed through the catalyst bed at a superficial velocity of 0.01 to 2.0 m/sec. Preferably, the lower limit of the superficial velocity is 0.014 m/sec, and the upper limit is 1.5 m/sec, and the metathesis reaction is performed at superficial velocities in this range.

The superficial velocity will be explained on the basis of the metathesis reaction on an industrial scale wherein a fixed bed flow reactor permitting easy separation of catalysts is used and a plug flow is produced. The superficial velocity (Uavg) is expressed by the following equation (1)

$$U\text{avg (m/sec)} = Fv/[\pi \times (Di/2)^2] \quad (1)$$

wherein Di is an inner diameter (m) of the reactor, and Fv is a feed rate (m³/sec) of the raw materials.

In more detail, the superficial velocity (Uavg) refers to the velocity of the gas (raw materials) passing through the metathesis catalyst and co-catalyst.

In the conventional metathesis reaction, the superficial velocity is low to make sure that the starting olefins will contact with the catalysts sufficiently. Therefore, the starting olefins are in contact with the metathesis catalyst and co-catalyst for a relatively long time. When hydrogen gas is present, the olefins are hydrogenated during such long contact time. This is probably a reason for the formation of paraffins to a considerable level.

The olefins are converted even if the contact time between the starting olefins and the metathesis catalyst and co-catalyst is greatly shortened. Any longer contact with the catalysts only invites the olefin hydrogenation forming paraffins. Based on this finding, the lower limit of the superficial velocity in the invention is fixed at a very high-speed level as compared with the conventional art. The upper limit of the superficial velocity ensures a minimum time required for the metathesis reaction to complete. If the superficial velocity is more than the upper limit, the contact between the starting olefins and the catalysts is insufficient and the metathesis reaction does not proceed sufficiently.

The superficial velocity is effective when the raw-material feeding rate per hour relative to the total catalyst weight (total weight of the metathesis catalyst and co-catalyst) (WHSV: 1/h) is in the range of 0.1 to 50 h⁻¹, and preferably in the range of 0.5 to 30 h⁻¹. If the raw-material feeding rate (WHSV) is below the lower limit, the contact time with the metathesis catalyst and co-catalyst is long, and more paraffins are by-produced. If the WHSV is above the upper limit, the metathesis reaction does not proceed sufficiently.

In the present invention, the starting olefins are preferably fed into the metathesis reactor with a small amount of hydrogen gas. The hydrogen gas may be added in an amount of 0.05 to 10% by volume, and preferably 0.08 to 5% by volume based on the total volume of the gas (total volume of the starting-olefins gas and the hydrogen gas). By introducing the hydrogen gas in such small amount, the metathesis catalysts maintain catalytic activity for a long time. If the amount of hydrogen is less than the above range, the catalytic activity may not be maintained. If the amount is more than described above, separating the unreacted hydrogen increases burdens. Even though the hydrogen gas is fed in the above amount, there is no significant increase in the amount of paraffins by-produced, and the metathesis catalysts maintain catalytic activity for a long time. This long-lasting activity of the metathesis catalysts probably contributes to the effective progress of the metathesis reaction at the superficial velocity in the above-mentioned range.

The hydrogen is generally supplied continuously in the gas state. In an embodiment of the invention, however, the hydrogen gas may be fed intermittently, i.e., the hydrogen gas may be added at the initiation of the metathesis reaction and the supply may be terminated during the reaction and may be restarted after a predetermined time.

In the invention, the starting olefins and the hydrogen gas are brought into contact with the metathesis catalyst and co-catalyst. The hydrogen gas may be recovered with low boiling fractions from the top of the tower and may be recycled.

As described above, hydrogen is used in the reducing treatment for the catalysts. If such hydrogen remains even after the reactor is purged with nitrogen, the residual hydrogen will help the metathesis catalysts maintain the activity at least in the very beginning of the reaction. However, the catalytic activity will be gradually reduced if hydrogen gas is not newly added, and the reaction results will be eventually equal to those obtained without adding hydrogen gas. In the olefin production by the metathesis reaction according to the present invention, the hydrogen gas is continuously supplied at a specific rate to the reaction system, and thereby the metathesis catalyst and co-catalyst can be used stably for a long time.

The reaction temperature is usually in the range of 100 to 500° C., and preferably in the range of 130 to 350° C. When the reaction temperature is extremely low, the reaction rate is lowered, and the productivity of the reaction products is decreased. When the reaction temperature is extremely high, side reactions occur to produce more by-products such as paraffins, and the catalyst deactivation is accelerated.

In the invention, the starting olefins and hydrogen are preheated to approximately 100 to 300° C., and are usually fed in the gas state to the reactor filled with the metathesis catalyst and co-catalyst.

The reaction pressure at the above temperature may be a reduced pressure, a superatmospheric pressure or atmospheric pressure. From the viewpoint of reaction efficiency (reaction efficiency per unit volume), the pressure is usually in the range of 0.01 to 20 MPa, and preferably in the range of 0.05 to 10 MPa. Under this pressure condition, the metathesis reaction will proceed smoothly. Excessively high pressures are disadvantageous in terms of facilities such as the need of reactors resistant to high pressures.

In the present invention, the olefin production by the metathesis reaction does not necessarily involve reaction solvents or diluting gases. However, the reaction system may include solvents or gases that are inert to the catalysts and the starting materials. Specific examples include alkanes such as methane, ethane, propane and butane, and inert diluting gases such as nitrogen and helium. Such components may be present in the reaction system, or may be added to the reaction system to control the reaction.

After the metathesis reaction, the reaction products are separated and recovered from the catalysts, the starting olefins, the hydrogen gas and the like. In detail, the target olefins are separated from the reaction mixture by a known method such as distillation, extraction or adsorption. The unreacted raw materials may be recovered and reused in the reaction system.

The metathesis reaction to produce olefins may be performed in any of the liquid phase, the gas phase and the gas-liquid mixed phase. Preferably, it is recommended that the reaction is carried out in the gas phase from the viewpoint of reaction efficiency.

In the olefin production of the present invention, a desired olefin output may be ensured by alternately using two or more reactors arranged in parallel in a manner such that the metathesis catalyst and co-catalyst in one reactor are regenerated with hot air or nitrogen-diluted air, while the olefins are produced by the metathesis reaction in the other reactor(s). This method is generally called a merry-go-round mode. By employing the merry-go-round mode, the olefins are produced more effectively. The reaction may involve three reactors, of which two reactors are connected in series to stabilize the production output. When the reaction is carried out in a fluidized-bed flow reaction mode or in a moving-bed reaction mode, the whole or part of the catalysts may be withdrawn from the reactor continuously or intermittently while newly adding a corresponding amount of the catalysts to maintain the activity at a certain level.

In the olefin production by the metathesis reaction, the metathesis catalyst and co-catalyst decrease their catalytic activity with time. The deactivated catalysts may be regenerated to recover the catalytic activity. In general, the olefins adsorbed on the catalysts are purged with nitrogen gas, and the catalysts are oxidized with air or nitrogen-diluted air at a temperature of 300° C. or higher. When the metal is tungsten or molybdenum, the catalysts are further subjected to reduction with a reducing gas such as hydrogen or carbon monoxide. The catalysts are thus reactivated.

EXAMPLES

The present invention will be described by Examples below without limiting the scope of the invention.

Example 1

8.3 g of ammonium metatungstate (Aldrich) was dissolved in 1 liter of distilled water, and 50 g of silica gel Q-10 available from Fuji Silysia Chemical Ltd. (surface area: 300 m$^2$/g, pore volume: 1 ml/g, 150 to 500 µm) was suspended in the solution. The suspension was stirred at room temperature for 30 minutes. Subsequently, water was evaporated in an evaporator.

The resulting white solid was calcined under an air atmosphere at 550° C. for 6 hours. The calcined product was referred to as the catalyst WQ-10.

Magnesium oxide (Kyowamag 150 (registered trademark) manufactured by Kyowa Chemical Industry Co., Ltd.), which was fine powder, was compressed with a hydraulic press at 200 kg/cm$^2$ for 3 minutes. The compact was then crushed and the particles were classified. The particles having diameters of 150 to 500 µm were used.

12 g of the catalyst WQ-10 and 48 g of the magnesium oxide were physically mixed and packed in the center of a SUS tube having an outer diameter of 18 mm, an inner diameter (Di) of 16 mm and a length of 1000 mm. The top and bottom of the tube were filled with α-alumina balls. A metathesis reactor was thus prepared.

The catalyst bed was 0.5 m high.

Prior to the metathesis reaction, the catalysts were pretreated in the following manner. Normal pressure nitrogen gas was supplied from the top of the reactor at a flow rate of 100 ml/min, and the temperature was raised to 500° C. and maintained constant for 1 hour. Subsequently, normal pressure hydrogen gas and nitrogen gas were fed at flow rates of 20 ml/min and 80 ml/min, respectively, at 500° C. for 30 minutes. Thereafter, nitrogen gas was supplied again at a flow rate of 100 ml/min at 500° C. for 2 hours. The temperature was then lowered to 300° C. while supplying the nitrogen gas.

Liquefied 1-butene (purity: 99%, manufactured by Mitsui Chemicals, Inc.) was purified by adsorption treatment with γ-alumina (NKHD-24, manufactured by Sumitomo Chemical Co., Ltd.).

After the pretreatment, ethylene and hydrogen were supplied at flow rates of 1.87 l/min and 31.6 ml/min, respectively, in terms of flow rates at 25° C. and normal pressure. The pressure inside the reactor was adjusted to 3.5 MPa via a back pressure valve.

The purified liquefied 1-butene was fed at 2.88 g/min to a preheater (200° C.) positioned upstream from the metathesis reactor. The gas of 1-butene from the preheater together with ethylene and hydrogen were supplied to the reactor to initiate the reaction.

In the reactor (300° C., 3.5 MPa), the feed rate (Fv) of the raw materials was $2.87 \times 10^{-6}$ m$^3$/sec. In other words, the weight hourly space velocity (WHSV) of the weight of the raw materials (g/h) to the total catalyst weight (g) was 5 h$^{-1}$. The hydrogen concentration in the raw materials was 1% by volume. The superficial velocity (Uavg) in the reactor was 0.014 m/sec from the following equation (1):

$$U\text{avg (m/sec)} = Fv/[\pi \times (Di/2)^2] \quad (1)$$

wherein Di was the inner diameter of the metathesis reactor, and Fv was the feed rate of the raw materials.

The pressure was adjusted to normal pressure via the back pressure valve, and the reaction products were automatically sampled. The sample was analyzed on-line by gas chromatography.

Based on the composition sampled 3 hours after the reaction initiation, the butene conversion was calculated to be 70% by deducting the total amount of trans-2-butene, cis-2-butene and 1-butene in the outlet gas from the amount of 1-butene supplied.

The propylene selectivity based on butene was 88%. Small amounts of pentene and hexene were also generated.

Of the hydrogen supplied, 20% was consumed in the by-production of ethane and propane. The reaction was continued for another 40 hours, but the butene conversion did not decrease.

In the above reaction carried out at a superficial velocity of 0.014 m/sec with addition of 1% by volume of hydrogen, the catalytic activity was maintained for a dramatically extended period of time, and the by-production of paraffins due to hydrogen was greatly suppressed.

Comparative Example 1

A metathesis reactor was prepared in the same manner as in Example 1, except that 0.6 g and 2.4 g of the catalyst WQ-10 and magnesium oxide used in Example 1 were physically mixed and packed in a SUS tube having an outer diameter of 18 mm, an inner diameter (Di) of 16 mm and a length of 400 mm. The catalysts were pretreated in the same manner as in Example 1.

The liquefied 1-butene treated by alumina adsorption was fed at a rate of 0.145 g/min, and ethylene was supplied at a flow rate of 87 ml/min in terms of flow rate at 25° C. and normal pressure. Hydrogen was not supplied. The raw-material gases were passed through the catalyst bed at 3.5 MPa and 300° C.

The weight hourly space velocity (WHSV) of the weight of the raw materials (g/h) to the total catalyst weight (g) was 5 h$^{-1}$. The hydrogen concentration in the raw materials was 0% by volume. The superficial velocity (Uavg) from the above equation (1) was 0.0007 m/sec.

The pressure was adjusted to normal pressure via the back pressure valve, and the reaction products were automatically sampled. The sample was analyzed on-line by gas chromatography.

Based on the composition sampled 1 hour after the reaction initiation, the butene conversion was calculated to be 70% by deducting the total amount of trans-2-butene, cis-2-butene and 1-butene in the outlet gas from the amount of 1-butene supplied. The propylene selectivity based on butene was 88%. Small amounts of pentene and hexene were also generated.

Although ethane or propane was not by-produced, the butene conversion decreased to 0% in 10 hours after the initiation of the reaction.

Comparative Example 2

The procedures of Comparative Example 1 were repeated except that a raw-material purifying device was positioned upstream from the preheater. The purifying device was a SUS tube (outer diameter: 18 mm, inner diameter (Di): 16 mm, length: 700 mm) filled with 6 g and 24 g of the catalyst WQ-10 and magnesium oxide respectively. Prior to the reaction, the catalysts in the purifying device were heated in the presence of nitrogen, then reduced with hydrogen, and heated again in the presence of nitrogen, and the temperature was lowered to ambient. The raw-material gas was passed through the purifying device and thereby impurities in 1-butene such as butadiene were completely removed by adsorption.

The pressure was adjusted to normal pressure via the back pressure valve, and the reaction products were automatically sampled. The sample was analyzed on-line by gas chromatography.

Based on the composition sampled 1 hour after the reaction initiation, the butene conversion was calculated to be 70% by deducting the total amount of trans-2-butene, cis-2-butene and 1-butene in the outlet gas from the amount of 1-butene supplied. The propylene selectivity based on butene was 88%. Small amounts of pentene and hexene were also generated. Ethane or propane was not by-produced, and the butene conversion did not decrease during 20 hours after the initiation of the reaction.

The results of Comparative Example 2 showed that by thoroughly removing the poisoning substances from the raw material butene, the catalysts remained active for an extended period of time. However, such thorough purification is too expensive to be performed on an industrial scale.

In the present invention, the raw material 1-butene is purified using γ-alumina, and the purified 1-butene is used in the metathesis reaction. If the raw material 1-butene is purified to a high level, the metathesis catalysts will remain active for a further extended period of time. However, purifying the raw materials adds large costs. Purification such as purification of 1-butene with γ-alumina in Example 1 can still allow for performing the metathesis reaction with industrial profitability.

Comparative Example 3

The procedures of Comparative Example 1 were repeated except that the hydrogen gas was fed in the metathesis reactor at a flow rate of 1.5 ml/min in terms of flow rate at 25° C. and normal pressure, i.e., the hydrogen concentration was 1% by volume relative to the raw materials.

Based on the composition sampled 3 hours after the reaction initiation, the butene conversion was calculated to be 70% by deducting the total amount of trans-2-butene, cis-2-butene and 1-butene in the outlet gas from the amount of 1-butene supplied. The propylene selectivity based on butene was 88%. Small amounts of pentene and hexene were also generated. Of the hydrogen supplied, 90% was consumed in the by-production of ethane and propane. The reaction was continued for another 20 hours, but the butene conversion did not decrease.

Comparative Example 4

The procedures of Comparative Example 3 were repeated except that the hydrogen gas was fed in the metathesis reactor at a flow rate of 0.7 ml/min, i.e., the hydrogen concentration was 0.5% by volume relative to the raw materials.

Based on the composition sampled 3 hours after the reaction initiation, the butene conversion was calculated to be 70% by deducting the total amount of trans-2-butene, cis-2-butene and 1-butene in the outlet gas from the amount of 1-butene supplied. The propylene selectivity based on butene was 88%. Small amounts of pentene and hexene were also generated. Of the hydrogen supplied, 90% was consumed in the by-production of ethane and propane. The reaction was continued for another 20 hours, but the butene conversion did not decrease.

From the above results, even though butadiene was not removed sufficiently from the raw material, the catalysts maintained the activity for an extended period of time by the addition of hydrogen. However, the addition of hydrogen also caused by-production of paraffins, which was not avoided simply by controlling the amount of hydrogen.

Comparative Example 5

The reaction was performed at 3.5 MPa and 300° C. in the same manner as in Comparative Example 1, except that the catalyst WQ-10 and magnesium oxide were used in amounts of 1.2 g and 4.8 g respectively, the liquefied 1-butene was fed at a rate of 0.29 g/min, and ethylene and hydrogen were supplied at flow rates of 180 ml/min and 3 ml/min respectively in terms of flow rates at 25° C. and normal pressure.

The weight hourly space velocity (WHSV) of the weight of the raw materials (g/h) to the total catalyst weight (g) was 5 $h^{-1}$. The hydrogen concentration in the raw materials was 1% by volume. The superficial velocity (Uavg) from the above equation (1) was 0.0014 m/sec.

Based on the composition sampled 3 hours after the reaction initiation, the butene conversion was calculated to be 70% by deducting the total amount of trans-2-butene, cis-2-butene and 1-butene in the outlet gas from the amount of 1-butene supplied. The propylene selectivity based on butene was 88%. Small amounts of pentene and hexene were also generated. Of the hydrogen supplied, 88% was consumed in the by-production of ethane and propane. The reaction was continued for another 20 hours, but the butene conversion did not decrease. From the above results, at an increased (compared to Comparative Example 1) superficial velocity of 0.0014 m/sec, the catalytic activity and the maintenance of catalytic activity were equivalent to those achieved according to the present invention; however, the by-production of paraffins due to hydrogen was not substantially suppressed.

Example 2

$WO_3/SiO_2$ and magnesium oxide were prepared according to the processes described in Example 1, then shaped. 180 g of the shaped $WO_3/SiO_2$ and 550 g of the shaped magnesium oxide were physically mixed and packed in a SUS tubular reactor having an outer diameter of 48.6 mm, an inner diameter (Di) of 41.2 mm and a length of 2 m. 240 g of the shaped magnesium oxide was further placed on the upper surface of the mixture. The top and bottom of the reactor were filled with α-alumina balls, and thereby the catalyst bed was fixed.

The catalyst bed was approximately 1 m high.

At normal pressure, nitrogen gas was supplied from the top of the reactor at a flow rate of 10.2 l/min, and the temperature was raised to 550° C. and maintained constant for about 10 hours. Subsequently, hydrogen gas and nitrogen gas were fed at flow rates of 1.5 l/min and 14.7 l/min, respectively, at 550° C. for 3 hours to reduce the catalysts. Thereafter, nitrogen gas was supplied again at a flow rate of 10.2 l/min at 550° C. for 24 hours. The temperature was then lowered to 300° C. (reaction temperature) while supplying the nitrogen gas.

The nitrogen gas was then switched to the reaction gas, which was supplied while controlling the internal pressure at 2.7 MPa via the back pressure valve. The reaction was thus initiated.

The reaction gas was composed of ethylene, a mixture of compounds with 4 carbon atoms (hereinafter, also referred to as the C4 mixture), and hydrogen. The C4 mixture contained 2-butenes (including cis-isomer and trans-isomer), 1-butene, isobutene, isobutane and n-butanes. The C4 mixture had a typical composition of which 50 to 60 wt % was accounted for by n-butenes, i.e., 2-butene and 1-butene.

Ethylene and the C4 mixture were supplied at flow rates of 2.1 kg/h and 4.7 kg/h respectively, and hydrogen was fed at a flow rate of 40 l/h in terms of flow rate at 25° C. and normal pressure. In the reactor (300° C., 2.7 MPa), the feed rate (Fv) of the raw materials was $7.6 \times 10^{-5}$ m$^3$/sec. In other words, the weight hourly space velocity (WHSV) of the weight of the raw materials (g/h) to the total catalyst weight (g) was 7 h$^{-1}$. The hydrogen concentration in the raw materials was 1% by volume. The superficial velocity (Uavg) from the above equation (1) was 0.055 m/sec.

The gas produced was sampled through a sampling line branched upstream from the back pressure valve, and was analyzed periodically by gas chromatography.

Based on the composition sampled 24 hours after the reaction initiation, the butene conversion was calculated to be 68.5% by deducting the total amount of 1-butene and 2-butene in the outlet gas from the total amount of 1-butene and 2-butene in the C4 mixture. Of the hydrogen supplied, 20% was consumed in the by-production of ethane and propane. The reaction was further continued, and the butene conversion was 58% after 500 hours after the initiation of the reaction.

Example 3

The procedures of Example 2 were repeated except that the hydrogen gas was fed in the metathesis reactor at a flow rate of 12 l/h in terms of flow rate at 25° C. and normal pressure, i.e., the hydrogen concentration was 0.3% by volume relative to the raw materials.

After 24 hours after the initiation of the reaction, the butene conversion was 68.5%. Of the hydrogen supplied, 20% was consumed in the by-production of ethane and propane. The reaction was further continued, and the butene conversion was 53% after 500 hours after the initiation of the reaction.

Example 4

The procedures of Example 2 were repeated except that the shaped magnesium oxide was replaced by a shaped product of magnesium oxide/aluminum oxide solid solution (MgO.Al$_2$O$_3$) obtained by calcination of hydrotalcite (the shaped product available from Mitsui Chemicals, Inc.).

After 24 hours after the initiation of the reaction, the butene conversion was 71%. Of the hydrogen supplied, 20% was consumed in the by-production of ethane and propane. The reaction was further continued, and the butene conversion was 65% after 500 hours after the initiation of the reaction.

Comparative Example 6

The procedures of Example 2 were repeated except that hydrogen was not added.

After 24 hours after the initiation of the reaction, the butene conversion was 70%. The butene conversion decreased to 40% during 500 hours after the initiation of the reaction.

From the results of Examples 2 to 4 and Comparative Example 6, the addition of hydrogen dramatically extended the durability of the catalytic activity, and the by-production of paraffins due to hydrogen was substantially suppressed at a superficial velocity of 0.055 m/sec.

INDUSTRIAL APPLICABILITY

In a process for producing olefins by a metathesis reaction comprising feeding an olefin gas to pass the olefin through a catalyst bed in the presence of hydrogen gas to convert the olefin into another kind of olefin, the catalyst bed comprising a catalyst including at least one metal selected from the group consisting of tungsten, molybdenum, rhenium, niobium, tantalum and vanadium, and a co-catalyst including a basic compound having at least one metal selected from the group consisting of Group Ia (alkali metals), Group IIa (alkaline earth metals), Group IIb and Group IIIa of the periodic table, the improvement comprises controlling the superficial velocity of the gas passing through the catalyst bed to 0.01 to 2.0 m/sec. According to the invention, target olefins are produced in high yields while side reactions forming paraffins are suppressed.

In the production of propylene according to the present invention as an example, the formation of propane which reduces the purity of propylene is suppressed. Moreover, ethane formation is also suppressed, and thus recycling the unreacted ethylene only results in minor concentration and accumulation of ethane in the system. In other words, the present invention does not require large amounts of energy for the separation of by-produced paraffins such as ethane, and olefins are produced safely and with superior advantages from process and economic standpoints.

The invention claimed is:

1. In a process for producing olefins by a metathesis reaction comprising feeding an olefin gas to pass the olefin through a catalyst bed in the presence of hydrogen gas to convert the olefin into another kind of olefin, the catalyst bed comprising a catalyst including at least one metal selected from the group consisting of tungsten, molybdenum, rhenium, niobium, tantalum and vanadium, and a co-catalyst including a basic compound having at least one metal selected from the group consisting of Group Ia (alkali metals), Group IIa (alkaline earth metals), Group IIb and Group IIIa of the periodic table, the improvement comprising controlling the superficial velocity of the gas passing through the catalyst bed to 0.01 to 2.0 m/sec.

2. The process according to claim 1, wherein the gas subjected to the metathesis reaction contains the hydrogen gas and the hydrogen gas accounts for 0.05 to 10.0% by volume of the total volume (100% by volume) of the gas.

3. The process according to claim 1, wherein the metathesis reaction is performed at 100 to 500° C.

4. A method of converting an olefin into another kind of olefin by a metathesis reaction while suppressing conversion of the olefin to paraffins, the method comprising:

feeding a gas of the olefin through a catalyst bed in the presence of hydrogen gas at 0.05 to 10.0% by volume of the total volume of the gas at a superficial velocity of the gas of 0.01 to 2.0 m/sec, the catalyst bed comprising a catalyst and a co-catalyst, the catalyst comprising at least one metal selected from the group consisting of tungsten, molybdenum, rhenium, niobium, tantalum, and vanadium, and the co-catalyst comprising a basic compound having at least one metal selected from the group consisting of Group Ia (alkali metals), Group IIa (alkaline earth metals), Group IIb and Group IIIa of the periodic table.

5. The method according to claim 4, wherein the metathesis reaction is performed at 100 to 500° C.

6. A method of selectively producing olefins, comprising:
converting an olefin into another kind of olefin by a metathesis reaction by feeding a gas of the olefin through a catalyst bed; and
suppressing conversion of the olefin to paraffins, wherein the gas of the olefin is fed through the catalyst bed in the presence of hydrogen gas at 0.05 to 10.0% by volume of the total volume of the gas at a superficial velocity of the gas of 0.01 to 2.0 m/sec, the catalyst bed comprising a catalyst and a co-catalyst, the catalyst comprising at least one metal selected from the group consisting of tungsten, molybdenum, rhenium, niobium, tantalum, and vanadium, and the co-catalyst comprising a basic compound having at least one metal selected from the group consisting of Group Ia (alkali metals), Group IIa (alkaline earth metals), Group IIb and Group IIIa of the periodic table.

7. The method according to claim 6, wherein the metathesis reaction is performed at 100 to 500° C.

* * * * *